US012240792B2

(12) United States Patent
Shiflett et al.

(10) Patent No.: US 12,240,792 B2
(45) Date of Patent: Mar. 4, 2025

(54) PROCESSES FOR THE PREPARATION OF ALKYLBENZENES

(71) Applicant: University of Kansas, Lawrence, KS (US)

(72) Inventors: Mark Brandon Shiflett, Lawrence, KS (US); Rajkumar Kore, Lawrence, KS (US); Aaron M. Scurto, Oskaloosa, KS (US)

(73) Assignee: Univeristy of Kansas, Lawrence, KS (US)

( * ) Notice: Subject to any disclaimer, the term of this patent is extended or adjusted under 35 U.S.C. 154(b) by 128 days.

(21) Appl. No.: 18/042,487

(22) PCT Filed: Aug. 20, 2021

(86) PCT No.: PCT/US2021/046822
§ 371 (c)(1),
(2) Date: Feb. 22, 2023

(87) PCT Pub. No.: WO2022/046537
PCT Pub. Date: Mar. 3, 2022

(65) Prior Publication Data
US 2023/0322646 A1  Oct. 12, 2023

Related U.S. Application Data

(60) Provisional application No. 63/069,271, filed on Aug. 24, 2020.

(51) Int. Cl.
C07C 2/62 (2006.01)
C07C 2/54 (2006.01)

(52) U.S. Cl.
CPC .......... *C07C 2/62* (2013.01); *C07C 2527/054* (2013.01); *C07C 2531/025* (2013.01)

(58) Field of Classification Search
None
See application file for complete search history.

(56) References Cited

U.S. PATENT DOCUMENTS 3,509,225 A   4/1970 Wotring et al.
4,298,547 A * 11/1981 Young ..................... C07C 4/06
                                               585/323

(Continued)

FOREIGN PATENT DOCUMENTS

DE   11 2004 001 729 T5   10/2006
WO   WO 2005/028446 A1    3/2005

(Continued)

OTHER PUBLICATIONS

Peng Cui et al., "Ionic liquid enhanced alkylation of iso-butane and 1-butene," *Catalysis Today* (2013), 200; pp. 30-35.

(Continued)

*Primary Examiner* — Tam M Nguyen
(74) *Attorney, Agent, or Firm* — Bell & Manning, LLC

(57) ABSTRACT

Processes for alkylating benzene are provided. In embodiments, the process comprises combining benzene, an olefin, and a catalyst composition under conditions to react benzene with the olefin to produce an alkylbenzene, the catalyst composition comprising components selected from the group consisting of an ionic liquid, an acid, and an aromatic; an acid, a base capable of forming an ionic liquid with the acid, and an aromatic; an ionic liquid and an acid; and an acid and a base capable of forming an ionic liquid with the acid. The ionic liquid does not comprise a metal halide and the catalyst composition is free of a metal halide and the aromatic, if present in the catalyst composition, is not the benzene being alkylated.

20 Claims, 7 Drawing Sheets

(56) References Cited

U.S. PATENT DOCUMENTS

| | | | |
|---|---|---|---|
| 5,043,508 A * | 8/1991 | Aufdembrink | B01J 29/049 585/455 |
| 5,824,832 A | 10/1998 | Sherif et al. | |
| 7,683,209 B2 | 3/2010 | Harmer et al. | |
| 8,283,492 B2 | 10/2012 | Harmer et al. | |
| 8,524,965 B2 | 9/2013 | Campbell et al. | |
| 10,246,395 B2 | 4/2019 | Rogers et al. | |
| 10,301,233 B2 | 5/2019 | Timken et al. | |
| 11,453,623 B2 * | 9/2022 | Weaver | C07C 2/70 |
| 2006/0014650 A1 * | 1/2006 | Campbell | C09K 8/584 166/305.1 |
| 2006/0178544 A1 * | 8/2006 | Murray | C10G 29/205 585/467 |
| 2008/0161619 A1 * | 7/2008 | Riley | C07C 2/66 585/446 |
| 2008/0293989 A1 * | 11/2008 | Khanmamedova | C07C 2/76 427/372.2 |
| 2010/0331599 A1 | 12/2010 | Subramaniam et al. | |
| 2015/0273460 A1 | 10/2015 | Buchbinder et al. | |
| 2016/0009612 A1 | 1/2016 | Riley et al. | |
| 2016/0060277 A1 | 3/2016 | Aduri et al. | |
| 2016/0168054 A1 | 6/2016 | Kalnes et al. | |
| 2018/0127335 A1 * | 5/2018 | Broderick | B01J 31/2208 |
| 2020/0239382 A1 * | 7/2020 | Bhattacharyya | C07C 2/70 |
| 2023/0322662 A1 | 10/2023 | Shiflett et al. | |
| 2023/0322663 A1 | 10/2023 | Shiflett et al. | |
| 2023/0373893 A1 | 11/2023 | Shiflett | |

FOREIGN PATENT DOCUMENTS

| | | | |
|---|---|---|---|
| WO | WO 2018/104875 A1 | 6/2018 | |
| WO | WO-2021097200 A1 * | 5/2021 | B01J 31/0227 |

OTHER PUBLICATIONS

Wikipedia, "Lewis acids and bases." May 22, 2019; retrieved from https://en.wikipedia.org/w/index.php?title=Lewis_acids_and_bases&oldid=898242465;pp. 1-10.

Congzhen Qiao et al., "Benzene alkylation with long chain olefins catalyzed by ionic liquids: a review," Front. Chem. Eng. China 2008, 2(3): 346-352. DOI 10.1007/x11705-008-0045-9.

Yibo He et al., "Synthesis of efficient SBA-15 immobilized ionic liquid catalyst and its performance for Friedel-Crafts reaction," *Catalysis Today* 276 (2016) 112-120.

PubChem SID 341662503—(imidazolium sulfonate), Sep. 2017; 8 pp.

J. Zhang et al., "Isobutane/2-butene alkylation catalyzed by chloroaluminate ionic liquids in the presence of aromatic additives," *Journal of Catalysis* 249 (2007) 261-268.

Rajkumar Kore et al., ZSM-5 Zeolite Nanosheets with Improved Catalytic Activity Synthesized Using a New Class of Structure-Directing Agents, *Chemistry A European Journal* 2014, 20, 1-12. DOI: 10.1002/chem.201402665.

Rajkumar Kore et al., "Synthesis of Dicationic Ionic Liquids and their Application in the Preparation of Hierarchical Zeolite Beta," *Chemistry A European Journal* 2011, 17, 14360-14365. DOI: 10.1002/chem.201102946.

Rajkumar Kore et al., "Replacing HF or AlCl3 in the Acylation of Isobutylbenzene with Chloroaluminate Ionic Liquids," *ACS Sustainable Chem. Eng.* 2020, 8, 10330-10334.

The International Search Report and Written Opinion issued on Dec. 6, 2021 for international patent application No. PCT/US21/46822; pp. 1-8.

E. Campaigne et al., "Simultaneous Vicinal Dichlorination," *J. Am. Chem. Soc.* (Jan. 1950), 72, 1; 629-630.

Chatel, et al., "Mixing ionic liquids—"simple mixtures" or "double salts"?," Green Chemistry, 2014, pp. 2051-2083, vol. 16, DOI: 10.1039/c3gc41389f.

Berton, et al., "Stripping Uranium from Seawater-Loaded Sorbents with the Ionic Liquid Hydroxylammonium Acetate in Acetic Acid for Efficient Reuse," Industrial & Engineering Chemistry Research, 2016, pp. 4321-4327, vol. 55, DOI: 10.1021/acs.iecr.5b03996.

Tang, et al., "Improved 1-butene/isobutane alkylation with acidic ionic liquids and tunable acid/ionic liquid mixtures," Journal of Catalysis, 2009, pp. 243-250, vol. 268. doi: 10.1016/j.jcat.2009.09.022.

* cited by examiner

TRIAZOLIUM

CHOLINE

PHOSPHONIUM CHOLINE

GUANIDINIUM

ISOQUINOLINIUM

QUINOLINIUM

SULFONIUM

PHOSPHONIUM

AND

AMMONIUM

CATIONS:

FORMULA A $[C_{R1}C_n im]^+$ (n=0-18; R1=H OR ALKYL GROUP)

FORMULA B $[C_{R1}Im-C_n-SO_3H]^+$ (n=0,3,4,5; R1=H OR ALKYL GROUP)

FORMULA C $[X_{R1R2R3}-C_n-SO_3H]^+$ (n=0,3,4,5; X=N,P,S; $R_1/R_2/R_3$=H, ALKYL GROUP)

FORMULA D

[PYRIDINIUM]$^+$ $R_2/R_3/R_4$=H, ALKYL GROUP $R_1$=H, ALKYL GROUP, $C_n$-SO$_3$H(n=0,3,4,5)

FORMULA E (n=0,1; m=0,1,2)
$R_1/R_2/$=H, ALKYL GROUP, $C_n$-SO$_3$H(n=0,3,4,5)

BASES:

FORMULA F n=0 TO 18

FORMULA G n=0,3,4,5

FORMULA H n=0,3,4,5; X=N,P,S;
$R_1/R_2$=H, ALKYL GROUP

FORMULA I $R_2/R_3/R_4$=H, ALKYL GROUP

FORMULA J n=0,1; m=0,1,2
$R_1$=H, ALKYL GROUP,
$C_n$-$SO_3H$(n=0,3,4,5)

PROCESSES FOR THE PREPARATION OF ALKYLBENZENES

CROSS-REFERENCE TO RELATED APPLICATIONS

The present application is a National Stage of International Application No. PCT/US21/46822, filed Aug. 20, 2021, which claims priority to U.S. provisional patent application No. 63/069,271 that was filed Aug. 24, 2020, the entire contents of both of which are incorporated herein by reference.

BACKGROUND

Linear alkylbenzenes (LABs) are an important intermediate in the detergent industry. Since the 1960s, LABs have emerged as the dominant precursor of biodegradable detergents. Commercially, mixtures of $C_{10}$ to $C_{13}$ olefins and benzene are contacted with either HF or $AlCl_3$, acids which catalyze the alkylation of benzene to produce a mixture of $C_{10}$ to $C_{13}$ alkylbenzenes. The HF-process is commercially dominate despite the risk of environmental contamination and other drawbacks such as equipment corrosion, difficult separation, and low selectivity (e.g., 14-20%) to certain alkylbenzenes such as $C_6H_5$—$(H_3C)CH(C_{10}H_{21})$ (2-LAB). Existing commercial processes also generally require large benzene:olefin ratios.

SUMMARY

The present disclosure provides processes for the preparation of alkylbenzenes, including linear alkylbenzenes.

Processes for alkylating benzene are provided. In embodiments, the process comprises combining benzene, an olefin, and a catalyst composition under conditions to react benzene with the olefin to produce an alkylbenzene, the catalyst composition comprising components selected from the group consisting of an ionic liquid, an acid, and an aromatic; an acid, a base capable of forming an ionic liquid with the acid, and an aromatic; an ionic liquid and an acid; and an acid and a base capable of forming an ionic liquid with the acid. The ionic liquid does not comprise a metal halide and the catalyst composition is free of a metal halide and the aromatic, if present in the catalyst composition, is not the benzene being alkylated.

In embodiments, a process for alkylating benzene comprises combining benzene, a linear alpha olefin or a mixture of linear alpha olefins, and a catalyst composition under conditions to react benzene with the olefin or the mixture to produce an alkylbenzene, the catalyst composition comprising components selected from the group consisting of an ionic liquid, an acid, and an aromatic; and an acid, a base capable of forming an ionic liquid with the acid, and an aromatic. The ionic liquid does not comprise a halide and the catalyst composition is free of a halide and the aromatic is not the benzene being alkylated.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

DETAILED DESCRIPTION

Figure 1A:
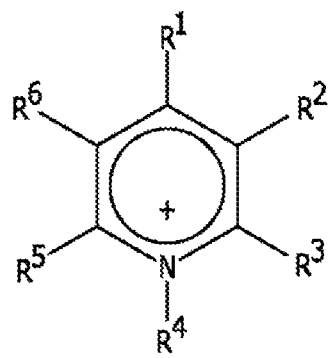
FIGS. 1A-1C show illustrative cations which may be used to form an ionic liquid for use in the present catalyst compositions.
Figure 1A:
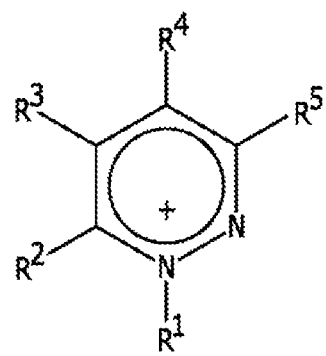
Figure 1A:
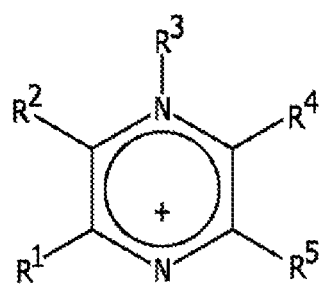
Figure 1A:
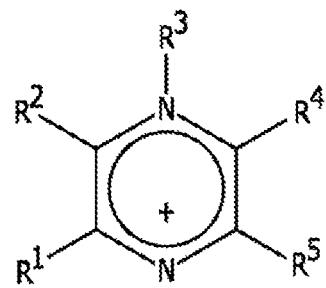
Figure 1A:
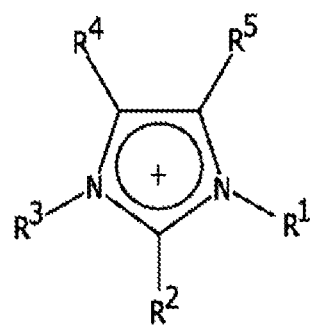
Figure 1A:
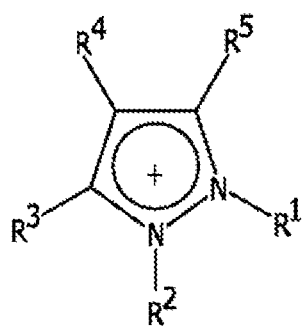
Figure 1A:
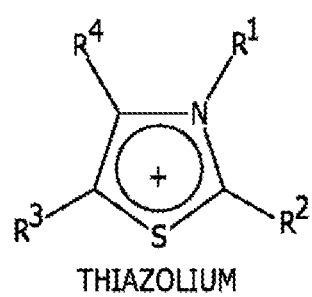
Figure 1A:
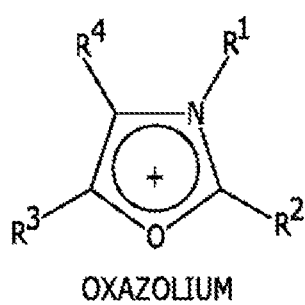

The present disclosure provides a process for the preparation of alkylbenzenes using certain catalyst compositions. At least some embodiments of the process achieve high conversion values (e.g., >99.9%), high selectivities to certain alkylbenzenes (e.g., 30-50% to 2-LAB), or both. The present processes are more environmentally friendly as compared to existing processes, e.g., those based on HF. Additional advantages include, but are not limited to, non-toxic and moisture stable catalyst composition, easy recovery of the catalyst composition, and tunable product selectivity via acidity of the catalyst composition.

The present catalyst compositions are multicomponent ionic systems which are typically liquids near room temperature (e.g., 20 to 25° C.). Components which may be used to form the catalyst compositions include certain ionic liquids; acids; bases; and aromatics. Each of these components are described below, followed by a description of various catalyst compositions formed therefrom.

Ionic Liquids

Various ionic liquids may be used to form the present catalyst compositions. As used in the present disclosure, "ionic liquid" refers to salts composed of at least one cation and at least one anion and are being used in their fluid state. They are generally in their fluid state at or below a temperature of about 100° C.

Representative examples of ionic liquids suitable for use herein are included among those that are described in sources such as J. Chem. Tech. Biotechnol., 68:351-356 (1997); Chem. Ind., 68:249-263 (1996); J. Phys. Condensed Matter, 5: (supp 34B):899-8106 (1993); Chemical and Engineering News, Mar. 30, 1998, 32-37; J. Mater. Chem., 8:2627-2636 (1998); Chem. Rev., 99:2071-2084 (1999); and WO 05/113,702 (and references cited therein), each of which is by this reference incorporated herein for the purpose of the ionic liquids disclosed therein.

Many ionic liquids are formed by reacting a nitrogen-containing heterocyclic ring, preferably a heteroaromatic ring, with an alkylating agent (e.g., an alkyl halide) to form a quaternary salt, and performing ion exchange or other suitable reactions with various Lewis acids or their conjugate bases to form the ionic liquid. Some ionic liquids are formed by reacting N-, P-, and S-compounds with a Bronsted acid to quaternize the heteroatom. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but the alkyl groups are preferably $C_{1-16}$ groups. Various trialkylphosphines, thioethers and cyclic and non-cyclic quaternary ammonium salts may also be used for this purpose. Ionic liquids suitable for use herein may also be synthesized by salt metathesis, by an acid-base neutralization reaction, or by quaternizing a selected nitrogen-containing compound. The synthesis of other ionic liquids suitable for use herein is described in U.S. Pat. No. 8,715,521, which is by this reference incorporated in its entirety as a part hereof for all purposes. Ionic liquids may also be obtained commercially from several companies such as Merck (Darmstadt, Germany), BASF (Mount Olive N.J.), Fluka Chemical Corp. (Milwaukee Wis.), and Sigma-Aldrich (St. Louis Mo.), Iolitec-Ionic Liquids Technologies, GmbH (Heilbronn, Germany) and Proionic (Graz, Austria).

Ionic liquids suitable for use herein comprise a cation and an anion. A variety of cations and anions may be used. Either or both of the ions may be fluorinated. However, in embodiments, neither of the ions are fluorinated. The ionic liquid may include more than one type of cation, more than one type of anion, or both. However, the ionic liquid may include a single type of cation and a single type of anion. When the ionic liquid includes a single type of cation and a single type of anion, however, this does not preclude some amount of ion exchange with other ions in the catalyst composition (derived from other components of the catalyst composition).

Figure 1B:
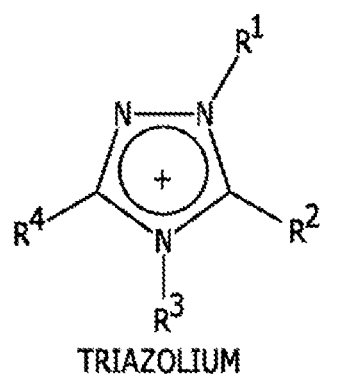
Figure 1B:
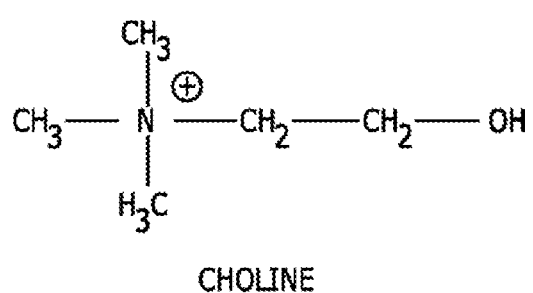
Figure 1B:
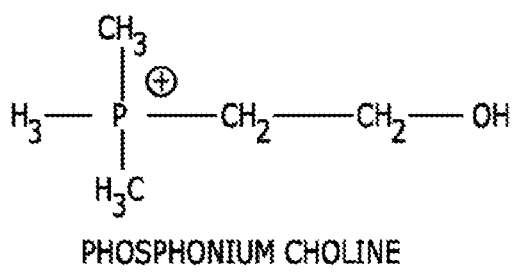
Figure 1B:
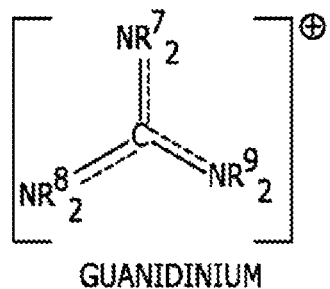
Figure 1C:
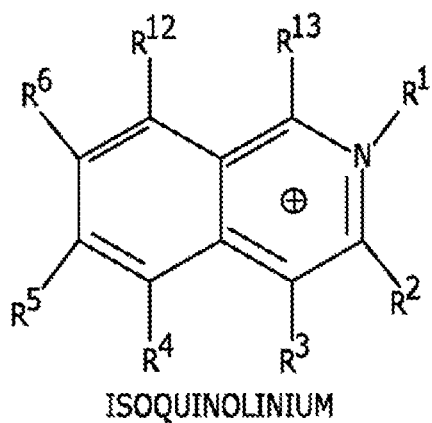
Figure 1C:
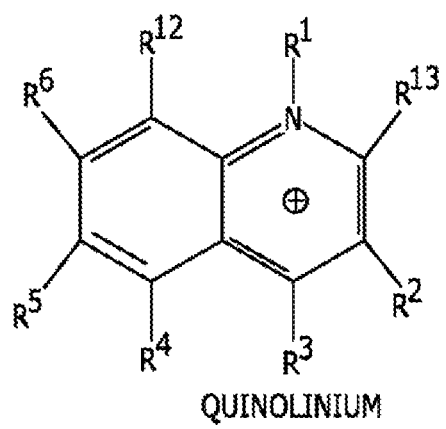
Figure 1C:
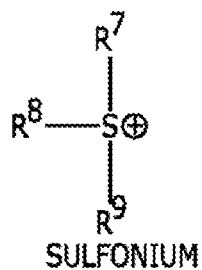
Figure 1C:
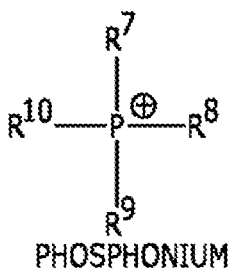
Figure 1C:
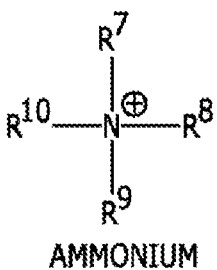

In embodiments, the cation is selected from the group consisting of cations represented by the structures of the formulae shown in FIGS. 1A-1C. In these formulae, the following provisos apply:

(a) $R^1, R^2, R^3, R^4, R^5, R^6, R^{12}$ and $R^{13}$ are independently selected from the group consisting of:
  (i) H;
  (ii) halogen such as F;
  (iii) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$ SH, and $SO_3H$;
  (iv) —$CH_3$, —$C_2H_5$, or $C_3$ to $C_{25}$ straight-chain, branched or cyclic alkane or alkene groups comprising one to three heteroatoms selected from the group consisting of O, N, Si and S, and optionally substituted with at least one member selected from the group consisting of Cl, Br, F, I, OH, $NH_2$ and SH;
  (v) $C_6$ to $C_{25}$ unsubstituted aryl, or $C_6$ to $C_{25}$ unsubstituted heteroaryl, groups having one to three heteroatoms independently selected from the group consisting of O, N, Si and S, wherein the unsubstituted aryl or unsubstituted heteroaryl may be bonded to the structure via an alkyl (e.g., —$CH_2$—) spacer group;
  (vi) $C_6$ to $C_{25}$ substituted aryl, or $C_6$ to $C_{25}$ substituted heteroaryl, groups having one to three heteroatoms independently selected from the group consisting of O, N, Si and S; wherein the substituted aryl or substituted heteroaryl may be bonded to the structure via an alkyl (e.g., —$CH_2$—) spacer group; and wherein said substituted aryl or substituted heteroaryl has one to three substituents independently selected from the group consisting of:
    (A) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$ and SH,
    (B) OH,
    (C) $NH_2$, and
    (D) SH; and
  (vii) —$(CH_2)_nSi(CH_2)_mCH_3$, —$(CH_2)_nSi(CH_3)_3$, —$(CH_2)_nOSi(CH_3)_m$, where n is independently 1-4 and m is independently 0-4;

(b) $R^7, R^1, R^9$, and $R^{10}$ are independently selected from the group consisting of:
  (i) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$, SH and $SO_3H$;
  (ii) —$CH_3$, —$C_2H_5$, or $C_3$ to $C_{25}$ straight-chain, branched or cyclic alkane or alkene groups comprising one to three heteroatoms selected from the group consisting of O, N, Si and S, and optionally substituted with at least one member selected from the group consisting of Cl, Br, F, I, OH, $NH_2$ and SH;
  (iii) $C_6$ to $C_{25}$ unsubstituted aryl, or $C_6$ to $C_{25}$ unsubstituted heteroaryl, groups having one to three heteroatoms independently selected from the group consisting of O, N, Si and S; and
  (iv) $C_6$ to $C_{25}$ substituted aryl, or $C_6$ to $C_{25}$ substituted heteroaryl, groups having one to three heteroatoms independently selected from the group consisting of O, N, Si and S, and wherein the substituted aryl or substituted heteroaryl group has one to three substituents independently selected from the group consisting of:
    (A) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$ and SH,
    (B) OH,
    (C) $NH_2$, and
    (D) SH; and
  (v) —$(CH_2)_nSi(CH_2)_mCH_3$, —$(CH_2)_nSi(CH_3)_3$, —$(CH_2)_n OSi(CH_3)_m$, where n is independently 1-4 and m is independently 0-4; and (c) optionally, at least two of $R^1, R^2, R^3, R^4, R^5, R^6, R^7, R^1, R^9$, and $R^{10}$ can together form a cyclic or bicyclic alkyl or alkenyl group.

In embodiments, the ionic liquid comprises a cation selected from one or more members of the group consisting of pyridinium, pyridazinium, pyrimidinium, pyrazinium, imidazolium, pyrazolium, thiazolium, oxazolium, triazolium, phosphonium, ammonium, benzyltrimethylammonium, choline, cholinium, dimethylimidazolium, guanidinium, phosphonium choline, lactam, sulfonium, tetramethylammonium, and tetramethylphosphonium.

In embodiments, the ionic liquid comprises an anion selected from one or more members of the group consisting of: $[CH_3CO_2]^-$, $[HSO_4]^-$, $[CH_3OSO_3]^-$, $[C_2H_5OSO_3]^-$, $[CH_3C_6H_4SO_3]^-$ ($[TSO]^-$), $[CO_3]^{2-}$, $[HCO_3]^-$, $[NO_2]^-$, $[NO_3]^-$, $[SO_4]_{2-}$, $[PO_3]^{3-}$, $[HPO_3]^{2-}$, $[H_2PO_3]^{1-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, carborates optionally substituted with alkyl or substituted alkyl; carboranes optionally substituted with alkylamine, substituted alkylamine, alkyl or substituted alkyl; and a fluorinated anion.

In embodiments, the ionic liquid comprises an anion selected from one or more members of the group consisting of aminoacetate, ascorbate, benzoate, catecholate, citrate, dimethylphosphate, formate, fumarate, glycolate, glyoxylate, iminodiacetate, isobutyrate, kojate, lactate, levulinate, oxalate, pivalate, propionate, pyruvate, salicylate, succinamate, succinate, tiglate, tetrafluoroborate, tetrafluoroethanesulfonate, tropolonate, $[CH_3CO_2]^-$, $[HSO_4]^-$, $[CH_3SO_3]^-$, $[CH_3OSO_3]^-$, $[C_2H_{50}SO_3]^-$, $[CH_3C_6H_4SO_3]^-$, $[CO_3]^{2-}$, $[HCO_3]^-$, $[NO_2]^-$, $[NO_3]^-$, $[SO_4]^{2-}$, $[PO_3]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[CHF_2CF_2CF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]^-$, $[CF_3CF_2OCF_2CF_2SO_3]^-$, $[(CF_2HCF_2SO_2)_2N]^-$, $[(CF_3CFHCF_2SO_2)_2N]^-$, $[N(CN)_2]$, $F^-$, and anions represented by the structure of the following formula, $[R_{11}COO]^-$, wherein $R^{11}$ is selected from the group consisting of:

(i) $—CH_3$, $—C_2H_5$, or $C_3$ to $C_{10}$ straight-chain, branched or cyclic alkane or alkene groups, optionally substituted with at least one member selected from the group consisting of Cl, Br, F, I, OH, $NH_2$ and SH;

(ii) $—CH_3$, $—C_2H_5$, or $C_3$ to $C_{10}$ straight-chain, branched or cyclic alkane or alkene groups that contain one to three heteroatoms selected from the group consisting of O, N, Si and S, and are optionally substituted with at least one member selected from the group consisting of Cl, Br, F, I, OH, $NH_2$ and SH;

(iii) $C_6$ to $C_{10}$ unsubstituted aryl, or $C_6$ to $C_{10}$ unsubstituted heteroaryl, groups having one to three heteroatoms independently selected from the group consisting of O, N, Si and S; and (iv) $C_6$ to $C_{10}$ substituted aryl, or $C_6$ to $C_{10}$ substituted heteroaryl, groups having one to three heteroatoms independently selected from the group consisting of O, N, Si and S; and wherein the substituted aryl or substituted heteroaryl group has one to three substituents independently selected from the group consisting of:

(A) $—CH_3$, $—C_2H_5$, or $C_3$ to $C_{10}$ straight-chain, branched or cyclic alkane or alkene groups, optionally substituted with at least one member selected from the group consisting of Cl, Br, F, I, OH, $NH_2$ and SH, (B) OH, (C) $NH_2$, and (D) SH.

Figure 1D:
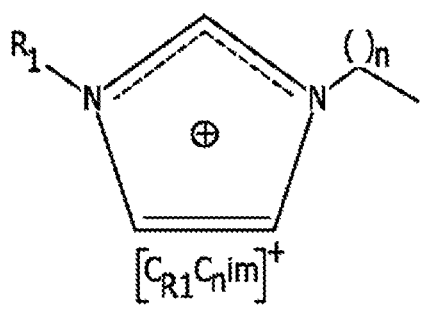
FIG. 1D shows illustrative cations which may be used to form an ionic liquid for use in the present catalyst compositions.
Figure 1D:
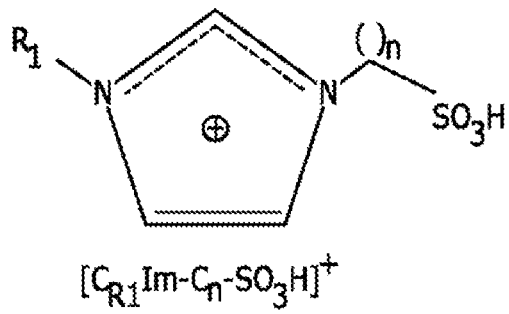
Figure 1D:
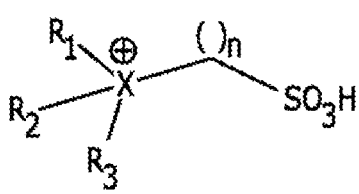
Figure 1D:
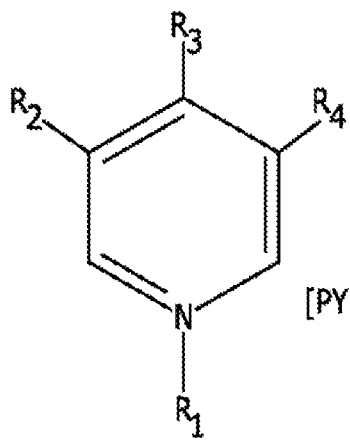
Figure 1D:
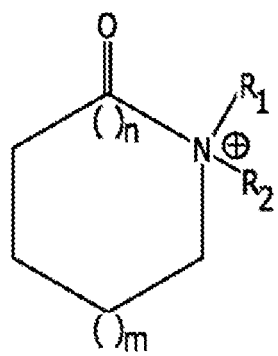

In embodiments, the cation of the ionic liquid is selected from an imidazolium, an ammonium, a phosphonium, a sulfonium, a pyridinium, and a lactam. The cation may be protic or aprotic. The proton in the protic cation may be from a $—SO_3H$ group. Illustrative imidazolium, ammonium, phosphonium, sulfonium, pyridinium, and lactam cations are shown in FIG. 1D. In embodiments, the cation of the ionic liquid is selected from the group consisting of cations represented by the structures of the formulae shown in FIG. 1D, i.e., Formulae A-E. In these formulae, the provisos noted in FIG. 1D apply.

In embodiments, the cation of the ionic liquid is an imidazolium having Formula A shown in FIG. 1D, an imidazolium having the formula shown in FIG. 1A, or an ammonium having the formula shown in FIG. 1C. In these formulae, the provisos noted in FIG. 1D and FIGS. 1A, 1C apply, respectively.

The anion of the ionic liquid may be a sulfonate. The sulfonate may have the formula $[R—SO_3]^-$, wherein R is an alkyl group or an aryl group. The alkyl group may be a linear alkyl group in which the number of carbons may range from, e.g., 1 to 12. The alkyl group may be unsubstituted, by which it is meant the alkyl group contains only carbon and hydrogen and no heteroatoms. The alkyl group may be substituted, by which it is meant an unsubstituted alkyl group in which one or more bonds to a carbon(s) or hydrogen(s) are replaced by a bond to non-hydrogen and non-carbon atoms. Non-hydrogen and non-carbon atoms include, e.g., a halogen atom such as F. Aryl groups may be unsubstituted or substituted as described above with respect to alkyl groups. However, substituted aryl groups also refer to an unsubstituted monocyclic aryl group in which one or more carbon atoms are bonded to an alkane. The alkane may be linear, have various numbers of carbon, and may be unsubstituted or substituted as described above with respect to alkyl groups.

Figure 2:
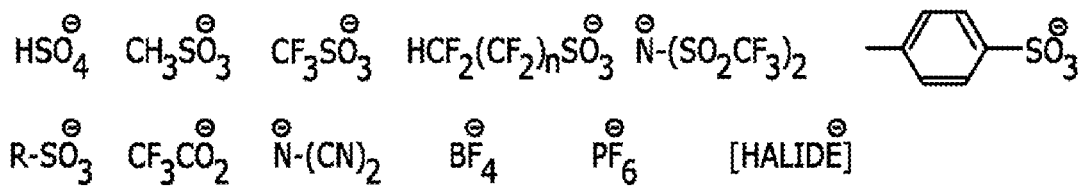
FIG. 2 shows illustrative anions which may be used to form an ionic liquid for use in the present catalyst compositions.

The anion may be a carboxylate. The carboxylate may have the formula $[R—CO_2]^-$, wherein R is an alkyl group as described above with respect to sulfonate. This means that fluoroalkane carboxylates are encompassed, e.g., R may be $CF_3$, $HCF_2CF_2$, $CF_3HFCCF_2$, etc. The carboxylate (or fluoroalkane carboxylate) may be a dicarboxylate, a tricarboxylate, a tetracarboxylate, etc. Other anions which may be used include $[HSO_4]$, dicyanamide; and inorganic anions such as $[BF_4]^-$, $[PF_6]^-$, and a halide. Illustrative anions are shown in FIG. 2. In $[HCF_2(CF_2)_nSO_3]^-$, n may be 0, 1, 2, or 3.

In embodiments, the anion of the ionic liquid is $[HSO_4]^-$ or $[HCF_2CF_2SO_3]^-$ Ionic liquids disclosed in the following references may also be used: U.S. Pat. Nos. 8,771,626; 8,779,220; 8,808,659; U.S. Pat. Pub. No. 20100331599; U.S. Pat. Nos. 7,432,408; 9,914,674; U.S. Pat. Pub. No. 20160289138; U.S. Pat. Pub. No. 20140113804; U.S. Pat. Pub. No. 20160167034; U.S. Pat. Pub. No. 20150315095; and U.S. Pat. Nos. 9,567,273; 9,346,042; 9,260,668; 9,096,487; 8,692,048; 8,653,318; 8,633,346; 8,569,561; 8,552,243; and 7,285,698. Each of these is by this reference incorporated herein for the purpose of the ionic liquids disclosed therein.

In the ionic liquids, various relative amounts of the cation(s) and anion(s) may be used. In embodiments, the molar ratio of the cation:anion is in the range of from 1:1 to 4:1.

Illustrative specific ionic liquids are also provided in the Examples, below.

In embodiments, the following provisos apply: the ionic liquid is not a haloaluminate (e.g., chloroaluminate), a halozincate, a haloferrate, a halogallate, a halostannate, a haloindate, a halochromate, a halocuprate, a halotitannate, a halozirconate, or a halopalladate and the ionic liquid is not formed from a metal halide (thus, neither the cation(s) nor the anion(s) of the ionic liquid are derived from such a metal halide). In such embodiments, the catalyst composition is free of such ionic liquids and free of a metal halide. In embodiments, the ionic liquid is not formed from a non-metal halide (thus, neither the cation(s) nor the anion(s) of the ionic liquid are derived from such a non-metal halide). In such embodiments, the catalyst composition is free of such ionic liquids and free of a non-metal halide. The term "halide" may be used to refer to both metal and non-metal halides. The embodiments in this paragraph do not preclude the use of certain halogenated cation(s), anion(s) (e.g., $HCF_2CF_2SO_3^-$), halogenated acids (e.g., haloalkane sulfonic acids), halogenated bases, and halogenated aromatic compounds (e.g., halogenated benzene). Throughout the present disclosure, the term "free" means that the amount of the relevant component is zero or sufficiently close to zero to have no material effect on the properties of the catalyst composition.

Known methods may be used to prepare ionic liquids. Other ionic liquids may be commercially available. Illustrative methods for synthesizing ionic liquids are described in the Examples, below.

Acids

Various acids may be used to form the present catalyst compositions, including combinations of different types of acids. However, a single type of acid may also be used. Mineral acids may be used, e.g., sulfuric acid, phosphoric acid, hydrofluoric acid, hydrochloric acid.

Sulfonic acids may be used. The sulfonic acid may have the formula R—SO$_3$H, wherein R is an alkyl group or an aryl group. The alkyl group may be linear, branched, or cyclic and may have a number of carbons in a range from, e.g., 1 to 12. The alkyl group may be unsubstituted, by which it is meant the alkyl group contains only carbon and hydrogen and no heteroatoms. The alkyl group may be substituted, by which it is meant an unsubstituted alkyl group in which one or more bonds to a carbon(s) or hydrogen(s) are replaced by a bond to non-hydrogen and non-carbon atoms. Non-hydrogen and non-carbon atoms include, e.g., a halogen atom such as F, Cl, Br, and I. Aryl groups may be unsubstituted or substituted as described above with respect to alkyl groups. However, substituted aryl groups also refer to an unsubstituted monocyclic aryl group in which one or more carbon atoms are bonded to an alkane. The alkane may be linear, branched, or cyclic, have various numbers of carbon atoms, and may be unsubstituted or substituted as described above with respect to alkyl groups.

Carboxylic acids may be used. The carboxylic acid may have the formula R—CO$_2$H, wherein R is an alkyl or an aryl group as described above with respect to sulfonic acid.

Figure 3:
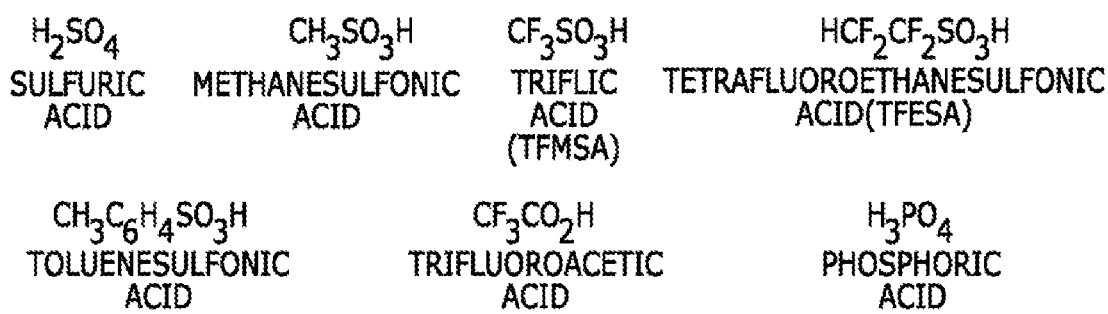
FIG. 3 shows illustrative acids for use in the present catalyst compositions.

Illustrative specific acids are shown in FIG. 3. In embodiments, the acid is triflic acid. In embodiments, the acid is sulfuric acid. In embodiments, the acid is tetrafluoroethanesulfonic acid.

In embodiments, the acid is not hydrofluoric acid and the catalyst composition is free of hydrofluoric acid.

Bases

In embodiments, a base is used which forms, in situ, an ionic liquid or a dissolved salt when combined with any of the disclosed acids in forming the catalyst composition. Thus, any base which generates any of the cations described in "Ionic Liquids," above, upon combination with any of the disclosed acids may be used. By way of illustration, the base may be an imidazole, an ammonia, a phosphine, a sulfide, a pyridine, or a lactam. The base be selected from the group of compounds having any of the formulae shown in FIG. 1E, i.e., Formulae F-J. In these formulae, the alkyl group may be a linear alkyl group in which the number of carbons may range from, e.g., 1 to 12. The alkyl group may be unsubstituted, by which it is meant the alkyl group contains only carbon and hydrogen and no heteroatoms. The alkyl group may be substituted, by which it is meant an unsubstituted alkyl group in which one or more bonds to a carbon(s) or hydrogen(s) are replaced by a bond to non-hydrogen and non-carbon atoms. Non-hydrogen and non-carbon atoms include, e.g., a halogen atom such as F.

Figure 1E:
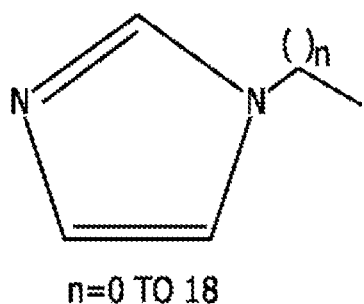
FIG. 1E shows illustrative bases for use in the present catalyst compositions.
Figure 1E:
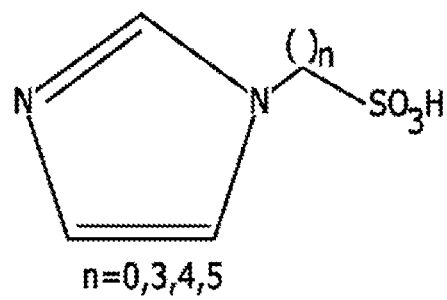
Figure 1E:
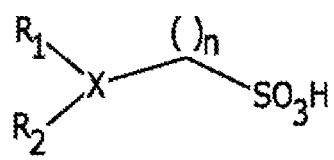
Figure 1E:
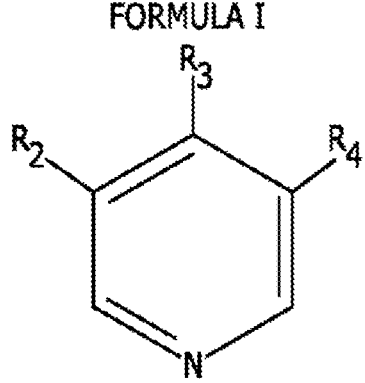
Figure 1E:
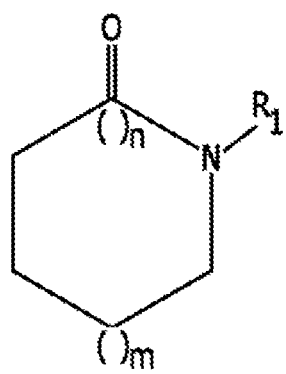

In embodiments, the base is an imidazole, e.g., having Formula F in FIG. 1E. In embodiments, the base is an ammonia.

The catalyst composition may be formed from different types of bases. However, a single type of base may also be used.

Aromatics

Various aromatics may be used to form the present catalyst compositions, including combinations of different types of aromatics. However, a single type of aromatic may also be used.

The aromatic may be monocyclic having one or more unfused aromatic rings. Each aromatic ring may have various members, e.g., a 5-membered ring, a six-membered ring, etc. Monocyclic aromatics may be unsubstituted, by which it is meant the aromatic contains only carbon and hydrogen and no heteroatoms. Unsubstituted monocyclic aromatics have a single aromatic ring. Monocyclic aromatics may be substituted, by which it is meant an unsubstituted aromatic in which one or more bonds to a carbon(s) or hydrogen(s) are replaced by a bond to non-hydrogen and non-carbon atoms. Non-hydrogen and non-carbon atoms include, e.g., a halogen atom such as F, Cl, Br; O; N; etc. However, substituted monocyclic aromatics also refer to an unsubstituted monocyclic aromatic in which one or more carbon atoms are bonded to an unsubstituted or substituted alkane or another unsubstituted or substituted monocyclic aromatic. The alkane may be linear or branched, have various numbers of carbon atoms, and may be unsubstituted or substituted as described above with respect to the definition of alkyl groups in "Acids." Thus, monocyclic aromatics include benzene, biphenyl, triphenyl, furan, pyridine, pyrrole, etc. (each which may be unsubstituted or substituted).

Figure 4:
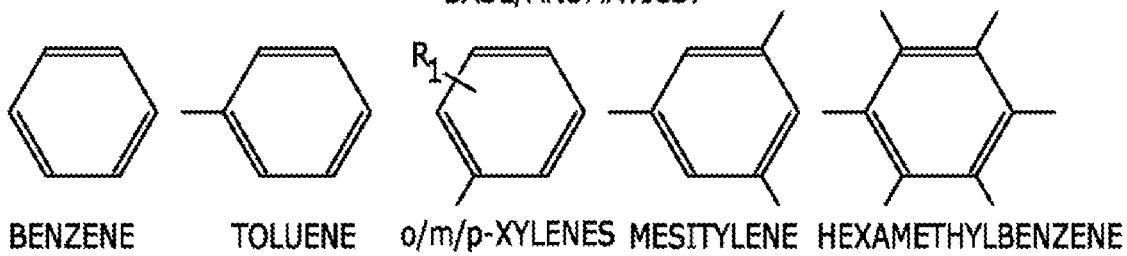
FIG. 4 shows illustrative aromatics for use in the present catalyst compositions.

The monocyclic aromatic may have the formula C$_6$R$_6$, wherein each R is independently selected from hydrogen, a halogen, and an alkyl group. The alkyl group may be linear or branched have various numbers of carbon atoms and may be unsubstituted or substituted as described above with respect to the definition of alkyl groups in "Acids." Illustrative such monocyclic aromatics are shown in FIG. 4.

Polycyclic aromatics may be used. Polycyclic aromatics have fused aromatic rings (e.g., two, three, etc. rings). Each ring may have various members and may be unsubstituted or substituted as described for monocyclic aromatics. Naphthalene, anthracene, phenanthrene, benzofuran are illustrative polycyclic aromatics.

In embodiments, the aromatic is benzene. In embodiments, the aromatic is hexamethylbenzene.

Similar to the bases described above, it is noted that the aromatic used in the catalyst composition may be one which forms, in situ, an ionic liquid when combined with the acid to form the catalyst composition.

Catalyst Compositions

One or more of any of the disclosed ionic liquids, acids, bases, and aromatics may be used to form the present catalyst compositions. As noted above, ion exchange generally occurs between the various components of the catalyst compositions, once formed. In addition, there may be some overlap between compounds suitable for the various components, e.g., some compounds may be suitable as a base and an aromatic. However, catalyst compositions described as comprising, e.g., an "ionic liquid," an "acid", and an "aromatic" refer to catalyst compositions in which separate and distinct chemicals have been combined to form the catalyst composition regardless of how the various ions may subsequently rearrange/associate therein. For example, a catalyst composition described as comprising an "ionic liquid," an "acid", and an "aromatic" means that a chemically distinct ionic liquid, a chemically distinct acid, and a chemically distinct aromatic were combined to form the catalyst composition. As another example, a catalyst composition described as comprising an ionic liquid and an acid refers to compositions in which a chemically distinct ionic liquid and a chemically distinct acid were combined to form the catalyst composition.

The particular component or combination of components may be selected to achieve certain behavior, e.g., desired conversion or desired product selectivity. Specific combinations are illustrated in the Examples below, but these are not intended to be limiting. Similarly, for catalyst compositions comprising more than one component, the components may be present at various amounts selected to achieve certain behavior. By way of illustration, as shown in the Examples, below, it has been found that both conversion and product selectivity are particularly sensitive to the type and amount of the acid component used. (See Table 2.)

Table 1, below, lists catalyst compositions which may be used. The various components may be selected from those described above. More than one type of each component may be used, i.e., more than one type of ionic liquid/base, more than one type of acid, and/or more than one type of aromatic. In other such embodiments, a single type of each component may be used. The provisos described above may apply, e.g., no metal halides; no hydrofluoric acid. The parameters x and y refer to weight percents, as further described below.

TABLE 1

Catalyst Compositions.

$[IL]_x$-$[Acid]_{(100-x)}$
$[IL]_x$-$[Acid]_{(100-x)}$-$[Aromatic]_y$
$[Base]_x$-$[Acid]_{(100-x)}$
$[Base]_x$-$[Acid]_{(100-x)}$-$[Aromatic]_y$ In the catalyst compositions $[IL]_x$–$[Acid]_{100-x}$ and $[Base]_x$-$[Acid]_{(100-x)}$, the parameter x refers to a weight (wt) %, i.e., ((weight of the ionic liquid/base)/(combined weight of the ionic liquid/base and the acid))*100. In embodiments, x is in a range of from 0.5 wt % to 90 wt % and the acid is present at an amount in a range of from 99.5 wt % to 10 wt %. This includes embodiments in which the ionic liquid/base is present at an amount in a range of from 2 wt % to 80 wt %, from 5 wt % to 60 wt %, from 5 wt % to 30 wt % or from 5 wt % to 20 wt % and the acid is present at an amount in a range of from 98 wt % to 20 wt %, from 95 wt % to 40 wt %, from 95 wt % to 70 wt % or from 95 wt % to 80 wt %, respectively.

In the catalyst compositions $[IL]_x$–$[Acid]_{(100-x)}$-$[Aromatic]_y$ and $[Base]_x$-$[Acid]_{(100-x)}$-$[Aromatic]_y$, x is as defined above and y refers to ((weight of the aromatic)/(combined weight of the ionic liquid/base, and acid))*100. In embodiments, the aromatic component may be present in any amount up to its saturation point in the composition. In embodiments, y is in a range of from of 0.1 wt % to 25 wt %. This includes from 1 wt % to 15 wt %, 1 wt % to 10 wt %, from 3 wt % to 9 wt %, or from 5 wt % to 8 wt %. In embodiments, y may be in a range of from 0.1 wt % to 100 wt % or from 0.1 wt % to 50 wt %.

An amount of water may be present in the catalyst composition. However, in embodiments, the catalyst composition consists or consists essentially of the components of Table 1.

Specific, illustrative catalyst compositions are provided in the Examples, below.

Other components may be included in the catalyst compositions such as multi-ammonium salts/surfactants described in R. Kore, B. Satpati, R. Srivastava, *Synthesis of Dicationic Ionic Liquids and their Application in the Preparation of Hierarchical Zeolite Beta, Chemistry—A European Journal,* 17 (2011) 14360-14365 and R. Kore, R. Srivastava, B. Satpati, *ZSM-5 zeolite nanosheets with remarkably improved catalytic activity synthesized using a new class of structure directing agents, Chemistry—A European Journal,* 20 (2014) 11511-11521, both of which are hereby incorporated by reference in their entirety.

The present catalyst compositions may be made by combining the desired components (together or sequentially) at the desired relative amounts. The synthesis may be carried out while stirring and under room temperature. Other details are provided in the Examples, below.

With regards to the present catalyst compositions comprising three components, an acid, an aromatic, and either an ionic liquid or a base which forms, in situ, an ionic liquid with the acid, the following is noted. Without wishing to be bound to any particular theory, it is believed that the three components (or ions generated from the three components) may associate to form a molecular complex having unique, synergistic properties, as distinguished from a simple mixture of the individual components. In the present disclosure, terms such as "ternary complex," "clathrate," and the like may be used to describe this molecular complex. However, such terms are not intended to limit the scope of structural form of the molecular complex or catalyst composition. The term "ternary mixture" may also be used in reference to the catalyst composition. Catalyst compositions comprising two components, e.g., an acid and an ionic liquid may be referred to as "binary mixtures."

LAB Process

The present catalyst compositions may be used in a process to alkylate benzene. In embodiments, such a process comprises combining benzene, an olefin, and any of the disclosed catalyst compositions under conditions to produce an alkylbenzene. Under the appropriate conditions, the present catalyst compositions can catalyze the addition of the olefin(s) to benzene to provide an alkylbenzene(s). The process may further comprise recovering the alkylbenzene(s) from the reaction mixture. Here, "benzene" refers to a benzene ring. The benzene ring may be unsubstituted or substituted. Unsubstituted benzene thus refers to $C_6H_6$. Substituted benzene refers to substituted monocyclic aromatics and polycyclic aromatics as described above in "Aromatics." The olefin may be a mono-olefin, including a linear alpha olefin. The number of carbon atoms in the olefin may be in the range of from 10 to 13. The olefin may be unsubstituted or substituted analogous to "alkyl" as described above in "Acids." Different types of olefins may be used in the process, i.e., a mixture of different types of olefins.

It is noted that the benzene to be alkylated may itself form a ternary complex with an acid and an ionic liquid/base in a catalyst composition used for the alkylation. However, when a catalyst composition is used for the alkylation which comprises any of the disclosed acids, an aromatic, and an ionic liquid or a base, the aromatic and the base, if present, are distinct chemical entities from the benzene to be alkylated. This means that either the aromatic/base are different chemical compounds from the benzene to be alkylated (i.e., are not benzene) or are the same chemical compound, but included separately at a separate amount in the catalyst composition.

The conditions under which the alkylation of benzene occurs refer to parameters such as the amount of the catalyst composition, the ratio of benzene:olefin, the reaction temperature, and the reaction time. These parameters may be adjusted to provide, e.g., a desired conversion and/or desired product selectivity. Illustrative values of these parameters are provided in the Examples below. Of course, the values may be scaled up as necessary for commercial processes.

Figure 5:
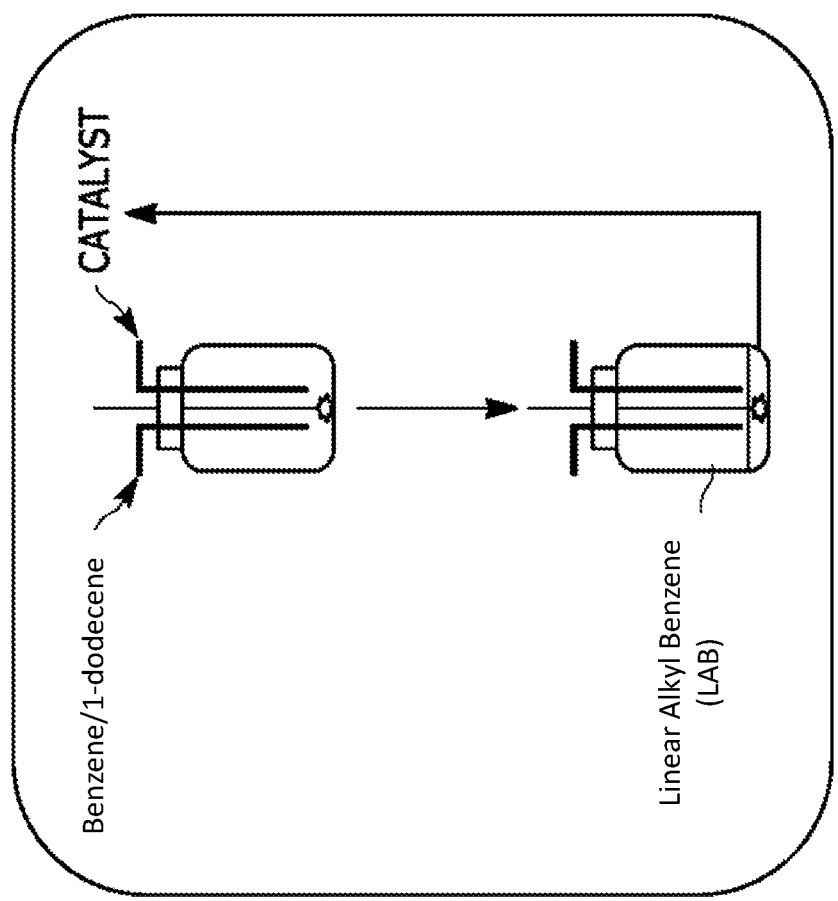
FIG. 5 is a schematic of a reaction system for carrying out a process for the preparation of alkylbenzenes using the present catalyst compositions.
Figure 6:
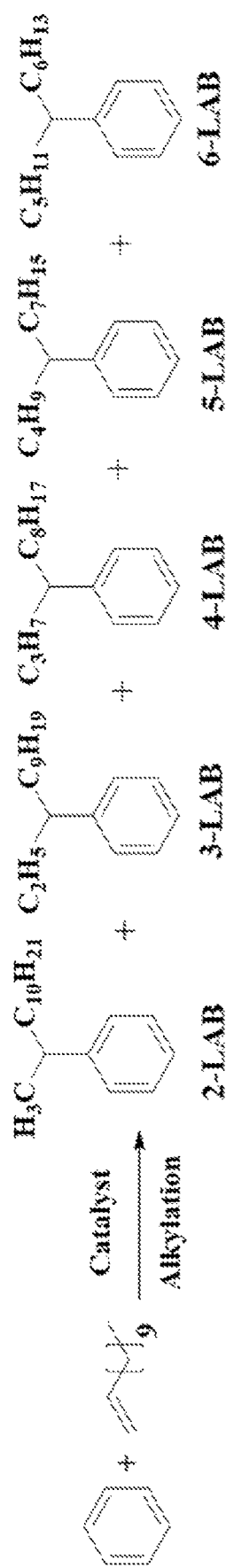
FIG. 6 shows the reaction scheme for the alkylation of benzene with 1-dodecene, which may be carried out using the present catalyst compositions.

A variety of reactor systems may be used to carry out the present processes, including batch, semi-continuous, continuous, and spray reactor systems. An illustrative system is shown in FIG. 5. Similarly, an illustrative process showing the alkylation of benzene with 1-dodecene is shown in FIG. 6.

The present catalyst compositions and alkylation processes may be characterized as being capable of achieving certain properties or results, including a percent conversion and a percent selectivity (for a particular product). Known methods may be used to calculate these values. In embodiments, the conversion is at least 99%, at least 99.5%, at least 99.9% or at least 100%. In embodiments, the selectivity for adding the olefin to benzene at its second carbon (e.g., 2-LAB) is at least 30%, at least 35%, at least 40%, at least 50%, or at least 60%. These properties may be referenced with respect to a particular set of reaction conditions, e.g., a set of reaction conditions as set forth in the Examples, below.

EXAMPLES

Example 1. Preparation of Ionic Liquids

Example 1-I: Preparation of N-methyl imidazolium hydrogen sulfate $[C_1im][HSO_4]$ IL In a 50 mL round bottom flask, equipped with a stir bar, an amount of N-methyl imidazole (4.11 g, 0.05 mol) was placed and then liquid $H_2SO_4$ acid (4.95 g, 0.05 mol) was added dropwise at 5° C. After addition, the reaction mixture was stirred at 80° C. for 4 h, giving a liquid IL $[C_1im][HSO_4]$.

Example 1-II: Preparation of triethylammonium heptachloro-dialuminate $[HN_{222}][Al_2Cl_7]$ IL In an Ar-filled glove bag, a 50 mL screw top borosilicate glass vial, equipped with a stir bar, an amount of triethylammonium chloride ($[HN_{222}][Cl]$) (0.05 mol) was placed and then solid $AlCl_3$ (0.1 mol) was added slowly. After addition, the reaction mixture was stirred at room temperature for 1 h, giving a liquid IL $[HN_{222}][Al_2Cl_7]$.

Example 2. Preparation of Binary Mixtures of an Ionic Liquid and an Acid

Example 2.1-I: Preparation of $([C_1C_4Im][HSO_4])_{10}$-$(TFMSA)_{90}$IL

In a 40 mL glass tube, equipped with a stir bar, TFMSA (2.25 g) and IL $[C_1C_4im][HSO_4]$ (0.25 g, commercially available) was added at 10:90 wt % and mixed by handshake. The reaction mixture was stirred at room temperature for 5 min, giving a liquid double salt IL $([C_1C_4im][HSO_4])_{10}$-$(TFMSA)_{90}$.

Example 2.1-II: Preparation of $([C_1C_4im][HSO_4])_{15}$-$(TFMSA)_{85}$ IL

In a 40 mL glass tube, equipped with a stir bar, TFMSA (2.13 g) and IL $[C_1C_4im][HSO_4]$ (0.38 g, commercially available) was added at 15:85 wt % and mixed by handshake. The reaction mixture was stirred at room temperature for 5 min, giving a liquid double salt IL $([C_1C_4im][HSO_4])_{15}$-$(TFMSA)_{85}$.

Example 2.1-III: Preparation of $([C_1C_4im][HSO_4])_{20}$-$(TFMSA)_{80}$ IL

In a 40 mL glass tube, equipped with a stir bar, TFMSA (2.0 g) and IL $[C_1C_4im][HSO_4]$ (0.20 g, commercially available) was added at 20:80 wt % and mixed by handshake. The reaction mixture was stirred at room temperature for 5 min, giving a liquid double salt IL $([C_1C_4im][HSO_4])_{20}$-$(TFMSA)_{80}$.

Example 2.2-I: Preparation of $([C_1C_4im][HSO_4])_{10}$—$(H_2SO_4)_{90}$ IL

In a 40 mL glass tube, equipped with a stir bar, $H_2SO_4$ (2.25 g) and IL $[C_1C_4im][HSO_4]$ (0.25 g, commercially available) was added at 10:90 wt % and mixed by handshake. The reaction mixture was stirred at room temperature for 5 min, giving a liquid double salt IL $([C_1C_4im][HSO_4])_{10}$—$(H_2SO_4)_{90}$.

Example 2.3-I: Preparation of $([N_{111-16}][HSO_4])_{10}$-$(TFMSA)_{90}$ IL

In a 40 mL glass tube, equipped with a stir bar, TFMSA (2.25 g) and IL $[N_{111-16}][HSO_4]$ (0.25 g, hexadecyltrimethyl ammonium hydrogen sulfate commercially available) was added at 10:90 wt % and mixed by handshake. The reaction mixture was stirred at room temperature for 5 min, giving a liquid double salt IL $([N_{111-16}][HSO_4])_{10}$-$(TFMSA)_{90}$.

Example 3. Preparation of Ternary Mixtures of an Ionic Liquid, an Acid, and an Aromatic Example 3.1-I: Preparation of $([C_1C_4im][HSO_4])_{10}$-$(TFMSA)_{90}$-$(HMB)_{10}$ Clathrate In a 40 mL glass tube, equipped with a stir bar, TFMSA (2.25 g) and IL $[C_1C_4im][HSO_4]$ (0.25 g) were added at 10:90 wt % and mixed by handshake. After a minute, 10 wt % of hexamethylbenzene (HMB; 0.25 g) was added and the reaction mixture was stirred at room temperature for 5 min, giving a liquid double salt IL clathrate $([C_1C_4im][HSO_4])_{10}$-$(TFESA)_{90}$-$(HMB)_{10}$.

Example 3.2-I: Preparation of $([C_1C_4im][HSO_4])_{10}$-$(TFMSA)_{90}$-$(Benzene)_{10}$ Clathrate In a 40 mL glass tube, equipped with a stir bar, TFMSA (2.25 g) and IL $[C_1C_4im][HSO_4]$ (0.25 g) were added at 10:90 wt % and mixed by handshake. After a minute, 10 wt % of Benzene (0.25 g) was added and the reaction mixture was stirred at room temperature for 5 min, giving a liquid double salt IL clathrate $([C_1C_4im][HSO_4])_{10}$-$(TFESA)_{90}$-$(Benzene)_{10}$.

Example 4. Linear Alkyl Benzene (LAB) Process Apparatus and Procedure

Alkylation of benzene/1-dodecene experiments were performed in a 40 mL borosilicate glass screw-top vial as shown in FIGS. 5 and 6. The benzene and 1-dodecene were premixed at 80:10 wt ratio and collected in syringe. The reaction mixture was analyzed offline by gas chromatography (GC), equipped with a flame ionization detector, and a DB-5 100 m column (J&W Scientific). Helium was used as the GC carrier gas and as the flame ionization detector (FID) makeup gas. The analysis conditions were: split ratio=50:1, injector temperature=280° C., detector temperature=300° C. carrier gas flow rate=20 sccm. The temperature program for GC analysis was as follows: initial column temperature 200° C./hold for 5 min, 10° C./min to 300° C./hold for 10 min.

All experiments were performed in batch. A typical experiment began with the addition of the catalyst into the 40 mL borosilicate glass screw-top vial equipped with a Teflon coated magnetic stir bar. The vial was sealed and heated to the desired temperature. The desired amount of premixed benzene/1-dodecene feed was injected into the vial while stirring the liquid phase. After a certain reaction time, stirring was stopped, and a small aliquot of mixture was withdrawn from the reaction mixture and monitored by using GC with FID. The results are shown in Table 2. As noted above, existing catalysts for the alkylation of benzene include acids such as HF and $AlCl_3$. The results of Table 2 show that dilution of other acids such as TFMSA and TFESA with ionic liquids and aromatics, surprisingly, does not negatively affect conversion and selectivity. Moreover, high conversions and high and tunable selectivities are achieved for non-metal halide based ionic liquids combined with acids and aromatics.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

If not already included, all numeric values of parameters in the present disclosure are proceeded by the term "about" which means approximately. This encompasses those variations inherent to the measurement of the relevant parameter as understood by those of ordinary skill in the art. This also encompasses the exact value of the disclosed numeric value and values that round to the disclosed numeric value.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use

TABLE 2

Alkylation of Benzene/1-dodecene reaction results.

| Catalyst | Catalyst Amount (g) | T (° C.) | Time min | Conv. (%) | Liquid Prod. Sel. (%) | | | | |
|---|---|---|---|---|---|---|---|---|---|
| | | | | | 2-LAB | 3-LAB | 4-LAB | 5-LAB | 6-LAB |
| Commercial HF-based process | | | | | 14-20 | | | | |
| Commercial $AlCl_3$ process | | | | | 26-33 | | | | |
| $AlCl_3$ (Present Application) | 0.5 | 30 | 10 | >99.9 | 33.0 | 19.2 | 15.6 | 15.9 | 15.1 |
| Literature data using $[HN_{222}][Al_2Cl_7]$ *Science China Chemistry*, 53: 1102-1107 (2010) | | | | | 39.3 | 19.8 | 13.9 | 13.8 | 13.2 |
| $[HN_{222}][Al_2Cl_7]$ (Present Application) | 0.5 | 30 | 10 | >99.9 | 39.9 | 20.8 | 13.4 | 13.0 | 12.8 |
| $[C_1C_4im][HSO_4]$ | 0.5 | 30 | 10 | Nil | — | — | — | — | — |
| TFMSA | 0.5 | 30 | 10 | >99.9 | 39.8 | 20.9 | 13.6 | 13.2 | 12.5 |
| | 0.15 | 30 | 10 | <0.5 | | | | | |
| $([C_1C_4im][HSO_4])_{10}$-$(TFMSA)_{90}$ | 0.2 | 30 | 10 | <0.5 | 54.4 | 17.2 | 10.4 | 8.7 | 9.3 |
| | 0.5 | 30 | 10 | >99.9 | 35.3 | 20.7 | 14.4 | 14.8 | 14.8 |
| $([C_1C_4im][HSO_4])_{15}$-$(TFMSA)_{85}$ | 0.5 | 30 | 10 | 66.3 | 38.6 | 21.1 | 14.0 | 13.6 | 12.7 |
| $([C_1C_4im][HSO_4])_{20}$-$(TFMSA)_{80}$ | 0.5 | 30 | 10 | 8.5 | 49.6 | 19.8 | 11.2 | 9.7 | 9.7 |
| | 0.5 | 45 | 10 | 37.1 | 41.8 | 20.5 | 12.1 | 12.7 | 11.9 |
| $([C_1C_4im][HSO_4])_{10}$-$(H_2SO_4)_{90}$ | 0.5 | 30 | 10 | 2.9 | 44.7 | 12.4 (13.1% extra) | 8.5 | 7.6 | 13.6 |
| $([N_{111(16)}][HSO_4])_{10}$-$(TFMSA)_{90}$ | 0.5 | 30 | 10 | >99.9 | 36.9 | 21.4 | 14.4 | 14.0 | 13.3 |
| $([C_1C_4im][HSO_4])_{10}$-$(TFMSA)_{90}$-$(HMB)_{10}$ | 0.5 | 30 | 10 | >99.9 | 38.3 | 20.7 | 15.3 | 17.3 | 8.4 |
| $([C_1C_4im][HSO_4])_{10}$-$(TFMSA)_{90}$-$(Benzene)_{10}$ | 0.5 | 30 | 10 | >99.9 | 35.6 | 20.7 | 14.3 | 14.7 | 14.7 |
| TFESA | 0.5 | 30 | 10 | >99.9 | 39.9 | 20.8 | 13.3 | 13.2 | 12.8 |
| $([C_1C_4im][HSO_4])_{10}$-$(TFESA)_{90}$ | 0.5 | 30 | 10 | 13.0 | 44.7 | 18.3 | 12.7 | 12.2 | 12.0 |
| $([C_1C_4im][HSO_4])_2$-$(TFESA)_{98}$ | 0.5 | 30 | 10 | >99.9 | 39.9 | 13.3 | 13.3 | 13.1 | 12.8 |
| $([C_1im-SO_3H][TFES])_{10}$-$(TFESA)_{90}$ | 0.5 | 30 | 10 | 36.8 | 42.3 | 22.0 | 12.6 | 11.8 | 11.3 |
| $([C_1im-SO_3H][TFES])_5$-$(TFESA)_{95}$ | 0.5 | 30 | 10 | 66.5 | 42.3 | 20.9 | 12.9 | 12.2 | 11.6 |
| $([C_1im-SO_3H][TFES])_2$-$(TFESA)_{98}$ | 0.5 | 30 | 10 | >99.9 | 39.4 | 20.8 | 13.5 | 13.2 | 13.0 |
| $([C_1im-SO_3H][TFES])_2$-$(TFESA)_{98}$-$(HMB)_2$ | 0.5 | 30 | 10 | >99.9 | 39.7 | 20.7 | 13.4 | 13.2 | 12.9 |
| $([C_1im-SO_3H][TFES])_2$-$(TFESA)_{98}$-$(HMB)_6$ | 0.5 | 30 | 10 | >99.9 | 39.4 | 20.7 | 13.5 | 13.4 | 12.8 |
| $([Im-(SO_3H)_2][TFES])_2$-$(TFESA)_{98}$ | 0.5 | 30 | 10 | >99.9 | 39.9 | 21.2 | 13.5 | 12.9 | 12.4 |
| $([N_{111-12}][HSO_4])_2$-$(TFESA)_{98}$ | 0.5 | 30 | 10 | >99.9 | 39.2 | 21.3 | 13.6 | 13.2 | 12.6 |

Reaction condition: Catalyst, 1-dodecene (1.68 g; 10 mmol), Benzene (6.2 g; 80 mmol), 30° C., 10 min.
Note:
TFMSA = Triflic acid; TFESA = Tetrafluoroethane-sulfonic acid; HMB = hexamethylbenzene.

What is claimed is:

1. A process for alkylating benzene, the process comprising combining benzene, an olefin, and a catalyst composition under conditions to react benzene with the olefin to produce an alkylbenzene, the catalyst composition comprising components selected from the group consisting of
   (a) an ionic liquid, an acid, and an aromatic; and
   (b) an acid, a base capable of forming an ionic liquid with the acid, and an aromatic;
   wherein the ionic liquid does not comprise a metal halide and the catalyst composition is free of a metal halide and the aromatic is not the benzene being alkylated.

2. The process of claim 1, wherein the ionic liquid does not comprise a non-metal halide and the catalyst composition is free of a non-metal halide.

3. The process of claim 1, wherein the aromatic is selected from an unsubstituted or substituted monocyclic aromatic.

4. The process of claim 1, wherein the aromatic has formula $C_6R_6$, wherein each R is independently selected from hydrogen, a halogen, and an unsubstituted or substituted alkyl group.

5. The process of claim 1, wherein the aromatic is selected from benzene, toluene, xylenes, mesitylene, hexamethylbenzene, and a halogenated benzene.

6. The process of claim 1, wherein the acid is triflic acid, $H_2SO_4$, or tetrafluoroethane sulfonic acid.

7. The process of claim 1, wherein the ionic liquid comprises an ammonium cation and the ammonium cation has formula $NR_4^+$, wherein each R is independently selected from alkyl groups.

8. The process of claim 1, wherein the ionic liquid comprises an imidazolium cation and the imidazolium cation has Formula A

wherein $R_1$ is hydrogen or alkyl and n is from 0 to 18.

9. The process of claim 1, wherein the ionic liquid comprises an imidazolium cation and the imidazolium cation has Formula B

wherein $R_1$ is hydrogen or alkyl and n is 0, 3, 4, or 5.

10. The process of claim 9, wherein n is 0.

11. The process of claim 1, wherein the ionic liquid comprises $[HSO_4]^-$ or $[HCF_2CF_2SO_3]^-$ as an anion.

12. The process of claim 1, wherein the ionic liquid comprises a cation selected from an ammonium and an imidazolium and $[HSO_4]^-$ or $[HCF_2CF_2SO_3]^-$ as an anion.

13. A process for alkylating benzene, the process comprising combining benzene, a linear alpha olefin or a mixture of linear alpha olefins, and a catalyst composition under conditions to react benzene with the olefin or the mixture to produce an alkylbenzene, the catalyst composition comprising components selected from the group consisting of
   (a) an ionic liquid, an acid, and an aromatic; and
   (b) an acid, a base capable of forming an ionic liquid with the acid, and an aromatic;
   wherein the ionic liquid does not comprise a metal halide and the ionic liquid does not comprise a non-metal halide and the catalyst composition is free of a metal halide and the catalyst composition is free of a non-metal halide and the aromatic is not the benzene being alkylated.

14. The process of claim 13, wherein the aromatic is selected from benzene, toluene, xylenes, mesitylene, hexamethylbenzene, and a halogenated benzene.

15. The process of claim 14, wherein the acid is triflic acid, $H_2SO_4$, or tetrafluoroethane sulfonic acid.

16. The process of claim 15, wherein the ionic liquid comprises a cation selected from an ammonium and an imidazolium and $[HSO_4]^-$ or $[HCF_2CF_2SO_3]^-$ as an anion.

17. The process of claim 1, wherein the acid is present in the catalyst composition at an amount in a range of from 80 weight % to 98 weight %, wherein weight % refers to (weight of the ionic liquid or the base)/(combined weight of the acid with the weight of the ionic liquid or the base)*100.

18. The process of claim 16, wherein the acid is present in the catalyst composition at an amount in a range of from 80 weight % to 98 weight %, wherein weight % refers to (weight of the ionic liquid or the base)/(combined weight of the acid with the weight of the ionic liquid or the base)*100.

19. The process of claim 1, wherein the aromatic is a halogenated benzene.

20. The process of claim 18, wherein the aromatic is a halogenated benzene.

* * * * *